United States Patent [19]

Aranguren Duo

[11] 4,261,342

[45] Apr. 14, 1981

[54] PROCESS FOR INSTALLING MITRAL VALVES IN THEIR ANATOMICAL SPACE BY ATTACHING CORDS TO AN ARTIFICIAL STENT

[76] Inventor: Iker Aranguren Duo, Estraunza, 10-60, Bilbao, Spain

[21] Appl. No.: 53,205

[22] Filed: Jun. 29, 1979

[30] Foreign Application Priority Data

Oct. 26, 1978 [ES] Spain .................................... 474.582

[51] Int. Cl.³ ............................................. A61B 19/00
[52] U.S. Cl. ......................................... 128/1 R; 3/1.5
[58] Field of Search ......................... 3/1.5, 1; 128/1 R

[56] References Cited

U.S. PATENT DOCUMENTS 4,035,849  7/1977  Angell et al. ............................. 3/1.5

*Primary Examiner*—Robert W. Michell
*Assistant Examiner*—Thomas Wallen
*Attorney, Agent, or Firm*—Wenderoth, Lind & Ponack

[57] ABSTRACT

A process is provided for installing mitral valves in their anatomical space by attaching cords to an artificial stent. A new valve to be implanted, having a human or an animal nature, is subjected to a preparation which includes isolating any other tissue of the donor, to be subsequently sutured both to the periphery of the valvular zone and to the base of the stents forming the subvalvular zone, and finally covering such zones with an anti-rejecting prosthetic material. The formation of the stents can be totally artificial, in which case the tendinous cords which activate the valvules of the valve are fixed to stents made only and exclusively from a material immune to rejection. Such cords are attached to a biological body which is subsequently covered, by the suture, with an immune material.

3 Claims, 4 Drawing Figures

PROCESS FOR INSTALLING MITRAL VALVES IN THEIR ANATOMICAL SPACE BY ATTACHING CORDS TO AN ARTIFICIAL STENT

BACKGROUND OF THE INVENTION

The present invention is directed to a process for installing mitral valves in their anatomical space by attaching cords to an artificial stent.

As is well known, the mitral valve is housed between the left auricle and the left ventricle of the heart. Further, the mitral valve functions for retaining or permitting the flow of blood which reaches the described auricle from the lungs to flow to the described left ventricle.

Opening and closing of the mitral valve is determined by the contraction of the left ventricle in which stents, which are formed by tendinous cords, are inserted. The cords are, in turn, attached to the valvules which make up the valve itself and which open and close the blood vessel.

The described tendinous cords act on a determined area of the valves, so that the contractions of the ventricle determine the traction exerted by the described tendinous cords and, consequently, the activation of the described valvules.

According to the techniques which are presently known and used, implantations or replacements are made with prosthetic or completely artificial apparatus, or with bioprosthetic valves having an artificial part and a natural or biological part.

Summary of the Invention

The process for installing mitral valves of the present invention permits a new human or porcine mitral valve to be implanted as a replacement for a diseased valve, with the new valve having been previously prepared.

The preparation of the new valve consists of isolating any other selected tissue of the donor and subsequently suturing same to the periphery of the valvular zone, which is to be attached to the hollow edge from which the prior mitral valve was removed, and to the base of the stents which form the sub-valvular zone. The selected tissue is then covered with a material which is immune to rejection, so that once the described zones have been appropriately covered with the prosthetic or artificial anti-rejecting material, the valve which is to be implanted is in perfect condition and does not cause any future problems of incompatability.

The stents can be completely prosthetic or artificial. More particularly, the tendinous cords are attached to stents which are made only and exclusively from material which is immune to rejection, such as for example Dacron having previously studied the characteristics of the mitral valve to be replaced. The said stents can also be biological, in which case the tendinous cords are attached to a natural body which is covered, by the suture, with the rejection immune material.

In both cases, as previously described, a pre-operative study of the characteristics of each mitral valve which is to be replaced is necessary. The study includes such factions as distances, positioning, etc. In addition, there should be a wide variety of a series of valves available which have different characteristics, in order to save time and to reduce the number of attachment points to the zone where the stents of the prior mitral valve was attached.

Further, as previously described, the valves which are to be inserted can be of human origin, obtained from suitable donors, or can be of porcine eorigin, and should be attached in the same space in which the replaced valve was housed. This greater safety and hemodynamic effectiveness, since the new valve occupies the exact anatomical position in the heart of the patient.

When the stents used are completely prosthetic or artificial, each tendinous cord should be isolated in its implantation in the papillary muscles of the left ventricle. This is accomplished by dissecting the papillary muscles of the left ventricle so that all of them preserve the endocardiac perimeter, this particular detail making up the fundamental basis for this type of implantation. Furthermore, the distances and magnitudes between the cords should be conserved so that each one, or each group thereof, can be securely attached to a resistant artificial material, which is placed in a parallel position for its equidistant mounting. Once the bases of the cords have been placed in the artificial material by means of suitable sutures having a verified resistance, the remaining organic material between the cords is dissected.

The new positioning of the artificial stent in its natural position is simplified since a wide series of gauges are available before the operation and since the sutures which are suitable for the sub-valvular characteristics of each case, can be made by means of a reduced number of attachment points.

To complement the description which follows, and for a better understanding of the characteristics of the invention a set of drawings, is attached to the specification in which the following is shown.

BRIEF DESCRIPTION OF THE DRAWINGS

FIG. 1 is a side view of the mitral valve, showing the arrangement of the anterior valvule, the dissected left stent and the partially dissected right stent or aortic arch, with the papillary tissues, in which the bases of the tendinous cords are inserted, not completely removed.

FIG. 2 is a partial side view, showing the implantation of the tendinous cords by means of a suture, in the artificial material, which is immune to rejection, and which maintains the distances and magnitudes between the tendinous cords.

FIG. 3 is a detailed view of a stent in which the cords are already attached to the artificial material.

DETAILED DESCRIPTION OF THE INVENTION

Figure 4:
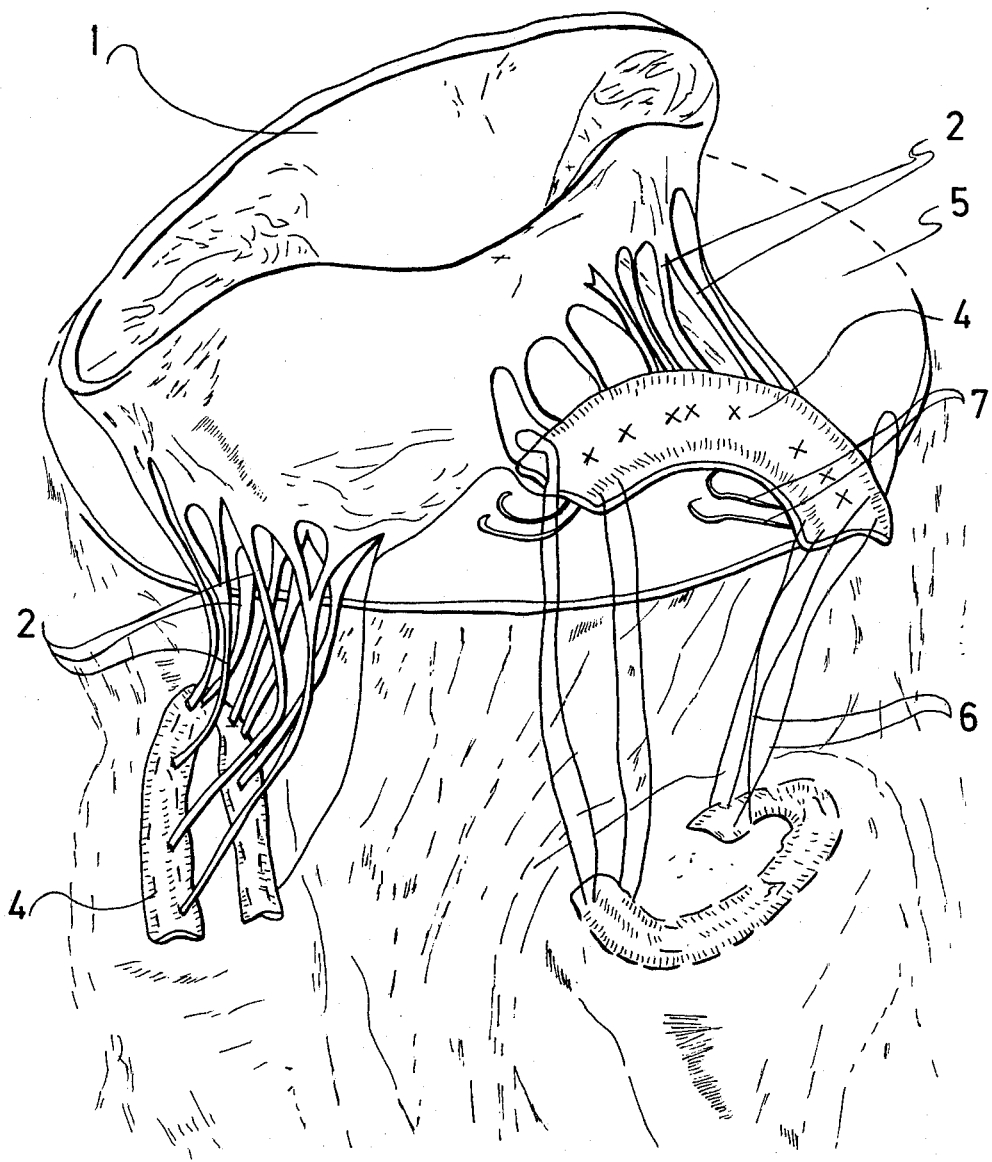
FIG. 4 shows the mitral valve with the two artificial stents, one of said stents being sutured to the posteromedial or aortic location, while the other is in the suturation phase, that is, at the time of suturing of the artificial antero-lateral stent in the location corresponding thereto.

It can be seen from the figures that the stents 3 are dissected from a mitral valve 1 which can be either human or animal. More particularly, the tissues corresponding to the appropriate locations of the other ventricle are isolated, separating the stents 3 from the tendinous cords 2 and suturing them, while maintaining the distances and magnitudes between them, to an artificial stent 4 which is obtained from a material which is immune to rejection.

Once the tendinous cords 2 are attached to the artificial stents 4, these stents 4 are sutured to the location provided therefor and from which the stents of the diseased mitral valve have been previously removed.

The joining to the location takes place after having verified the resistance of the sutures and the position corresponding thereto. Attachment takes place with threads 6 and clinical needles 7.

The endocardiac perimeter of the mitral valve 1 is then attached to the hollow edge 5 from which the prior mitral valve has been extracted. The endocardiac perimeter of the mitral valve having also previously been covered with an artificial material which is immune to rejection.

I claim:

1. A method of installing a mitral valve in an appropriate anatomical space in the heart of a patient, said method comprising the steps of:

providing a donor biological mitral valve, said valve having been selected to fit an appropriate anatomical space in the heart of the patient, said valve having been removed from said donor with tendinous cords attached thereto and said tendinous cords attached to appropriate sections of papillary muscle which have been removed from said donor;

providing stents which correspond in size and shape to the size and shape of said sections of the papillary muscles to which said tendinous cords are attached;

attaching said tendinous cords to said stents at locations on said stents corresponding to the locations on said sections of the papillary muscles to which said tendinous cords are attached;

covering said stents and the periphery of said biological mitral valve with an anti-rejecting prosthetic material; and suturing said stents and said periphery of said biological mitral valve to the corresponding part of the patient heart.

2. A method of installing a mitral valve as in claim 1 wherein said stents are made of artificial material which is immune to rejection.

3. A method of installing a mitral valve as in claim 1 wherein said stents are made of biological material supplied from the donor.

* * * * *